US00RE49518E

(19) United States
(12) Reissued Patent
Urano et al.

(10) Patent Number: US RE49,518 E
(45) Date of Reissued Patent: May 2, 2023

(54) FLUORESCENT PROBE FOR DETECTING CALPAIN ACTIVITY

(71) Applicants: The University of Tokyo, Tokyo (JP); Tohoku University, Miyagi (JP)

(72) Inventors: Yasuteru Urano, Tokyo (JP); Yuri Nagayo, Tokyo (JP); Mako Kamiya, Tokyo (JP); Toru Nakazawa, Miyagi (JP)

(73) Assignees: The University of Tokyo, Tokyo (JP); Tohoku University, Miyagi (JP)

(21) Appl. No.: 17/327,001

(22) Filed: May 21, 2021

Related U.S. Patent Documents

Reissue of:
(64) Patent No.: 10,294,240
Issued: May 21, 2019
Appl. No.: 15/553,970
PCT Filed: Feb. 29, 2016
PCT No.: PCT/JP2016/056030
§ 371 (c)(1),
(2) Date: Jan. 2, 2018
PCT Pub. No.: WO2016/137004
PCT Pub. Date: Sep. 1, 2016

(30) Foreign Application Priority Data

Feb. 27, 2015 (JP) ..... 2015-039502

(51) Int. Cl.
*C07D 493/10* (2006.01)
*A61K 49/00* (2006.01)
*C12Q 1/37* (2006.01)
*G01N 21/78* (2006.01)
*G01N 33/58* (2006.01)

(52) U.S. Cl.
CPC ..... *C07D 493/10* (2013.01); *A61K 49/00* (2013.01); *A61K 49/0041* (2013.01); *C12Q 1/37* (2013.01); *G01N 21/78* (2013.01); *G01N 33/582* (2013.01); *G01N 2333/96466* (2013.01); *G01N 2800/168* (2013.01)

(58) Field of Classification Search
CPC .. C07D 493/10; A61K 49/00; A61K 49/0041; C12Q 1/37; G01N 21/78; G01N 33/582; G01N 2333/96466; G01N 2800/168
See application file for complete search history.

(56) References Cited

U.S. PATENT DOCUMENTS 8,461,358 B2 * 6/2013 Nagano ..... C09B 11/24 435/15
9,506,102 B2 * 11/2016 Urano ..... C07D 493/10
9,610,366 B2 * 4/2017 Urano ..... A61K 49/0043
2007/0072807 A1 * 3/2007 Christie ..... A61K 38/10 514/160
2012/0052518 A1 3/2012 Nagano et al.
2013/0023675 A1 * 1/2013 Urano ..... A61K 49/0043 549/344
2014/0206992 A1 * 7/2014 Urano ..... A61K 49/0043 600/431
2015/0152469 A1 6/2015 Urano et al.
2016/0102336 A1 4/2016 Nagano et al.
2017/0073321 A1 * 3/2017 Urano ..... C07H 17/04
2017/0157272 A1 * 6/2017 Urano ..... A61K 49/0041

FOREIGN PATENT DOCUMENTS

WO WO 2010/095450 A1 8/2010
WO WO 2013/180181 A1 12/2013
WO WO 2014/136780 A1 9/2014
WO WO 2016/006678 A1 1/2016
WO WO2016006678 * 1/2016

OTHER PUBLICATIONS

Fujii, T., et al., In vivo Imaging of Intraperitoneally Disseminated Tumors in Model Mice by Using Activatable Fluorescent Small—Molecular Probes for Activity of Cathepsins, Bioconjugate Chemistry 25(10):1838-1846.
Glaucoma Clinical Practice Guidelines, 3rd Edition, copyright 2012, Japan Glaucoma Society, Chika Prefecture Matsudo-shi, Gokanishi.
Leytus, S.P., Rhodamine-based compounds as fluorogenic substrates for serine proteinases, Biochem. J. 209:299-307, 1983.
Mittoo, S., et al., Synthesis and Evaluation of Fluorescent Probes for the Detection of Calpain Activity, Analytical Biochemistry 319:234-238, Aug. 15, 2003.
O'Brien, M., et al., Light Up your Calpain Activity Calpain no Kassei Seibutsu Hakko Assay, Prometech Journal, No. 18, pp. 3-6, 2005.
Rosser, B.G., et al., Calpain Activity Increases in Hepatocytes Following Addition of ATP. Demonstration by a Novel fluorescent Approach, Journal of Biological Chemistry 268(31):23593-23600, 1993.

(Continued)

*Primary Examiner* — Jerry D Johnson
(74) *Attorney, Agent, or Firm* — Knobbe, Martens, Olson & Bear, LLP

(57) ABSTRACT

[Problem] To provide a fluorescent probe that detects calpain activity in cells at high sensitivity.
[Solution] A compound represented by the following general formula (I) or a salt thereof.

(I)

9 Claims, 11 Drawing Sheets

(56) References Cited

OTHER PUBLICATIONS

Rosser, B.G., et al., Cellular In Vivo Assay of Calpain Activity Using a Fluorescent Substrate, Methods in Molecular Biology, 144:245-259, 2000.
Sakabe, M., et al., Rational Design of Highly Sensitive Fluorescence Probes for Protease and Glycosidase Based on Precisely Controlled Spirocyclization, Journal of the American Chemical Society 135(1):409-414, 2013.
Shinkai-Ouchi, F., et al., Predictions of Cleavability of Calpain Proteolysis by Quantitative Structure-Activity Relationship Analysis Using Newly Determined Cleavage Sites and Catalytic Efficiencies of an Oligopeptide Array, Mol. Cell. Proteomics, 15:1262-1280, 2016.
Vanderklish, P.W., et al., Marking Synaptic Activity in Dendritic Spines With a Calpain Substrate Exhibiting Fluorescence Resonance Energy Transfer, PNAS 97(5):2253-2258, 2000.
Rosser; Methods in Molecular Biology 2000, 144, 245-259. (Year: 2000).*
Mittoo; Analytical Biochemistry 319 (2003) 234-238. (Year: 2003).*
Shinkai-Ouchi; Mol Cell Proteomics 2016, 15, 1262-1280. (Year: 2016).*
Leytus; Biochem. J. (1983) 209, 299-307. (Year: 1983).*
Sakabe; J. Am. Chem. Soc. 2013, 135, 409-414. (Year: 2013).*
Azuma, M., et al., Errata, Survey of Ophthalmology 53(3):308-310, 2008.
Blomgren, K., and J.-O. Karlsson, Calpain and Calpastatin Activity in the Optic Pathway, Neuroscience Letters 112:179-183, 1990.
Glaucoma Clinical Practice Guidelines, 3rd Edition, copyright 2012, Japan Glaucoma Society, Chika Prefecture Matsudo-shi, Gokanishi, X-Abs.
Huang, W., et al., Calpain Activation in Experimental Glaucoma, Investigative Ophthalmology & Visual Science 51(6):3049-3054, 2010.
International Search Report and Written Opinion issued in Application No. PCT/JP2016/056030 dated May 24, 2016.
McKernan, D.P., et al., A Key Role for Calpains in Retinal Ganglion Cell Death, Investigative Ophthalmology & Visual Science 48(12):5420-5430, 2007.
Nakajima, E., et al., Activation of the Mitochondrial Caspase Pathway and Subsequent Calpain Activation in Monkey RPE Cells Cultured Under Zinc Depletion, Eye 28:85-92, 2014.
Niapour, M., and S. Berger, Flow Cytometric Measurement of Calpain Activity in Living Cells, International Society for Analytical Cytology, Cytometry Part A 71A:475-485, 2007.
Osborne, N.N., et al., Retinal Ischemia: Mechanisms of Damage and Potential Therapeutic Strategies, Progress in Retinal and Eye Research 23:91-147, 2004.
Ozaki, T., et al., Inhibitory Peptide of Mitochondrial u-Calpain Protects Against Photoreceptor Degeneration in Rhodopsin Transgenic S334ter and P23H Rats, Plos One 8(8):1-10, 2013, www.plosone.org.
Ozaki, T., et al., Intravitreal Injection or Topical Eye-Drop Application of a μ-calpain C2L Domain Peptide Protects Against Photoreceptor Cell Death in Royal College of Surgeons' Rats, A Model of Retinitis Pigmentosa, Biochimica et Biophysica Acta 1822:1783-1795, 2012.
Persson, H., et al., Immunohistochemical Localization of Calpains and Calpastatin in the Rabbit Eye, Brain Research 611:272-278, 1993.
Shanab, A.Y., et al., Metabolic Stress Response Implicated in Diabetic Retinopathy: The Role of Calpain, and the Therapeutic Impact of Calpain Inhibitor, Neurobiology of Disease 48:556-567, 2012.
Suzuki, R., et al., Degeneration and Dysfunction of Retinal Neurons in Acute Ocular Hypertensive Rats: Involvement of Calpains, Journal of Ocular Pharmacology and Therapeutics 30(5):419-428, 2014.
Vanderklish, P.W., et al., Marking Synaptic Activity in Dendritic Spines With a Calpain Substrate Exhibiting Fluorescense Resonance Energy Transfer, PNAS 97(5):2253-2258, 2000.
Fujii, T., et al., In vivo Imaging of Intraperitoneally Disseminated Tumors in Model Mice by Using Activatable Fluorescent Small-Molecular Probes for Activity of Cathepsins, Bioconjugate Chemistry 25(10):1838-1846, Published Sep. 5, 2014.
Hinman, J.D., et al., Activation of Calpain-1 in Myelin and Microglia in the White Matter of the Aged Rhesus Monkey, Journal of Neurochemistry 89(2):430-441, 2004.
Liu, L., et al., μ-Calpain Regulates Caspase-Dependent and Apoptosis Inducing Factor-Mediated Caspase-Independent Apoptotic Pathways in Cisplatin-Induced Apoptosis, International Journal of Cancer 125(12):2757-2766, 2009.
O'Brien, M., et al., Light Up your Calpain Activity Calpain no Kassei Seibutsu Hakko Assay, Prometech Journal, No. 18, pp. 3-6, 2005, X-Abs.
Rosser, B.G. et al., Calpain Activity Increases in Hepatocytes Followiing Addition of ATP. Demonstration by a Novel fluorescent Approach, Journal of Biological Chemistry 268(31):23593-23600, 1993.
Ryu, M., et al. Critical role of Calpain in Axonal Damage-Induced Retinal Ganglion Cell Death, Journal of Neuroscience Research 90:802-815, 2012.
Barnett, E.M., et al., Single-Cell Imaging of Retinal Ganglion Cell Apoptosis With a Cell-Penetrating, Activatable Peptide Probe in an in Vivo Glaucoma Model, PNAS 106(23):9391-9396, Jun. 9, 2009.
Extended European Search Report received in connection with European Patent Application No. 16755748.7 dated Oct. 24, 2018.
Mitto, S., et al., Synthesis and Evaluation of Fluorescent Probes for the Detection of Calpain Activity, Analytical Biochemistry 319:234-238, Aug. 15, 2003.

* cited by examiner (a)Ac-LLY-HMRG (a)Ac-LM-HMRG (b)Ac-LM-HMRG+ALLN1μM (c)Ac-LM-HMRG+ALLN2μM (d)Ac-LM-HMRG+ALLN5μM (a) NMDA group, before Ac-LM-HMRG administration (b) NMDA group, 30 min after Ac-LM-HMRG administration (c) NMDA group, 60 min after Ac-LM-HMRG administration (d) NMDA group, 90 min after Ac-LM-HMRG administration (a) PBS group, before Ac-LM-HMRG administration (b) PBS group, 30 min after Ac-LM-HMRG administration (c) PBS group, 60 min after Ac-LM-HMRG administration (d) PBS group, 90 min after Ac-LM-HMRG administration (a) NMDA group, FG (b) NMDA group, Ac-LM-HMRG (c) NMDA group, Sytox Orange (dead cell stain)

(a) PBS group, FG (b) PBS group, Ac-LM-HMRG (c) PBS group, Sytox Orange (dead cell stain)

FLUORESCENT PROBE FOR DETECTING CALPAIN ACTIVITY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to a green fluorescent probe capable of detecting the activity of calpains. The present invention also relates to diagnostic for retinal disease that uses the fluorescent probe.

BACKGROUND ART

Glaucoma is the number one cause of acquired blindness in adults in Japan, affecting an average of approximately 5% of those at least 40 years old. The definition of glaucoma is "a disease characterized by functional, structural abnormality of the eye having characteristic changes in the optic nerve and visual field in which optic nerve damage can usually be improved or suppressed by lowering the intraocular pressure sufficiently" (Non-patent Reference 1). Glaucoma is broadly classified as I) primary glaucoma, II) secondary glaucoma, and III) developmental glaucoma. I) primary glaucoma is also classified as 1) glaucoma primary open-angle glaucoma (broad sense) (A: primary open-angle glaucoma, B: normotensive glaucoma), 2) primary closed-angle glaucoma (A: primary closed-angle glaucoma, B: iris plateau glaucoma), and 3) mixed glaucoma (Non-patent Reference 1).

Elevated intraocular pressure is one finding often seen in glaucoma, but in Japan normotensive glaucoma in which the intraocular pressure remains constantly at a normal value during the course of development and progress of the glaucoma accounts for approximately 70% of all glaucoma patients. This is a trend seen conspicuously in Asia. The treatment method for glaucoma currently relied upon, however, is only lowering the intraocular pressure, and treatment methods for factors other than intraocular pressure are being sought.

Glaucoma in all its forms is characterized by the progressive disappearance of retinal ganglion cells (RGC) and corresponding visual field abnormalities. The disappearance of RGC has recently been suggested to be affected by calpain activity, and disappearance of RGC is reported to be decreased by administration of a calpain inhibitor in an animal model of normotensive glaucoma (Non-patent Reference 2).

The participation of calpains is also suggested in retinitis pigmentosa (RP), age-related macular degeneration (AMD), and retinal neuropathy associated with diabetic retinopathy (Non-patent References 3-6).

Further, it is thought that calpain activation participates in retinal vascular occlusive diseases such as retinal vein occlusion and retinal artery occlusion, which are ischemic diseases (Non-patent References 7 and 8).

Calpains are cysteine proteases that act $Ca^{2+}$-dependently. They are expressed universally in the central nervous system and are related to neurodegenerative diseases such as Alzheimer's disease, Parkinson's disease, and Huntington's disease. Calpains are expressed by RGC and the nerve fiber layer in the retina (Non-patent References 9-11), and activation of calpains is confirmed in the GCL (ganglion cell layer) of retinal grafts after axotomy and in rat glaucoma models (Non-patent References 12 and 13). Calpains indirectly induce an apoptosis pathway, and, as a result, are related to the disappearance of RGC.

From this viewpoint, it is thought that being able to observe calpain activity in real time in animal models would make it possible to:

(1) clarify when, where, and how calpain activity participates in the pathology of retinal diseases and (2) use the knowledge of (1) to assess the progress of retinal diseases and the timing of treatment intervention.

Calpain probes reported to date are:

(A) a protein-based probe in which a fluorescent protein domain is bonded to a peptide that serves as a substrate of calpain (Non-patent Reference 14) and (B) a probe in which a dipeptide is bonded to coumarin (Non-patent Reference 15). However, the development of a calpain activity-detecting fluorescent probe that does not rely on gene introduction and does not use UV light for excitation light is required in imaging in live cells.

PRIOR ART REFERENCES

Non-Patent References

Non-Patent Reference 1: Japan Glaucoma Society HP.

Non-Patent Reference 2: M Ryu, M. Yasuda, D. Shi, A. Y Shanab, R. Watanabe, N. Himori, K. Omodaka, Y Yokoyama, J. Takano, T. Saido, T. Nakazawa, J Neurosci Res. 2012, 90, 802-815.

Non-Patent Reference 3: Eye (2014) 28, 85-92.

Non-Patent Reference 4: Biochimica et Biophysica Acta 1822 (2012) 1783-1795.

Non-Patent Reference 5: PLOS ONE August 2013, Volume 8, Issue 8, e71650.

Non-Patent Reference 6: Neurobiology of Disease 48 (2012) 556-567.

Non-Patent Reference 7: Retinal ischemia: Mechanisms of damage and potential therapeutic strategies. Osborne N N, Casson R J, Wood J P, Chidlow G, Graham M, Melena J. Prog Retin Eye Res. 2004 January; 23(1): 91-147.

Non-Patent Reference 8: Degeneration and dysfunction of retinal neurons in acute ocular hypertensive rats: Involvement of calpains. Suzuki R, Oka T, Tamada Y, Shearer T R, Azuma M. J Ocul Pharmacol Ther. 2014 June; 30(5): 419-28.

Non-Patent Reference 9: K. Blomgren, J. O. Karlsson, Neurosci. Lett. 1990, 112, 179-183.

Non-Patent Reference 10: H. Persson, S. Kawashima, J. O. Karlsson, Brain Res. 1993, 611, 272-278.

Non-Patent Reference 11: M. Azuma, T. R. Shearer, Surv. Ophthalmol. 2008, 53, 150-163.

Non-Patent Reference 12: D. P. McKernan, M. B. Guerin, O'Brien, C. J., T. G. Cotter, Invest. Ophthalmol. Vis. Sci. 2007, 48, 5420-5430.

Non-Patent Reference 13: W. Huang, J. B. Fileta, I. Rawe, J. Qu, C. L. Grosskreutz, Invest. Ophthalmol. Vis. Sci. 2010, 51, 3049-3054.

Non-Patent Reference 14: P. W. Vanderklish, L. A. Krushel, B. H. Hoist, J. A. Gally, K. L. Crossin, G. M. Edelman, Proc. Natl. Acad. Sci. U.S.A. 2000, 97, 2253-2258.

Non-Patent Reference 15: M. Niapour, S. Berger, Cytometry A. 2007, 71, 475-485.

SUMMARY OF THE INVENTION

Problems to be Solved by the Invention

The purpose of the present invention is to provide a fluorescent probe that detects calpain activity in cells at high sensitivity.

The purpose of the present invention is also to provide a diagnostic for retinal disease that, through the use of the fluorescent prove, permits real time monitoring of calpain activity and clarification of pathology, clinical diagnosis, and assessment of therapeutic effect in retinal neuropathy that progresses via activation of calpains in the field of ophthalmology.

Means for Solving the Problems

Upon in-depth studies, the present inventors discovered that a fluorescent probe the fluorescence of which rises during enzymatic reaction with calpains within cells can be provided by using HMRG as a basic skeleton and amide bonding a peptide chain to serve as a substrate for calpains, and completed the present invention.

Specifically, the present invention provides:

[1] A compound of the following general formula (I):

[Chemical formula 1]

(I)

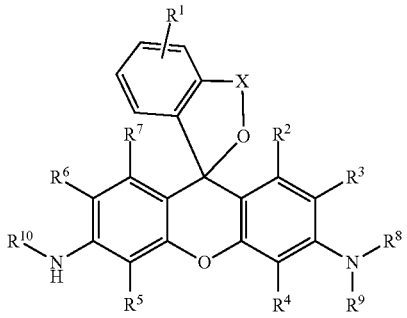

wherein $R^1$ is a hydrogen atom or from one to four of the same or different substituents that bond to the benzene ring;

$R^2$, $R^3$, $R^4$, $R^5$, $R^6$, and $R^7$ are, each independently, a hydrogen atom, hydroxyl group, alkyl group, or halogen atom;

$R^8$ and $R^9$ are, each independently, a hydrogen atom or alkyl group;

X is a $C_1$-$C_3$ alkylene group;

$R^{10}$ is a monovalent substituent cleaved by contact with calpain;

or a salt thereof.

[2] The compound according to [1] wherein $R^{10}$ is a monovalent substituent including an oligopeptide residue, or a salt thereof.

[3] The compound according to [2] wherein the monovalent substituent including an oligopeptide residue is represented by the following formula (1) or (2), or a salt thereof.

(1)

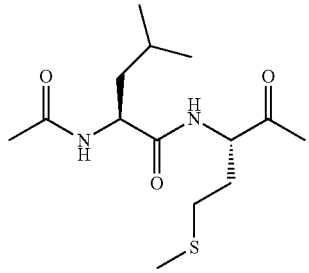

(2)

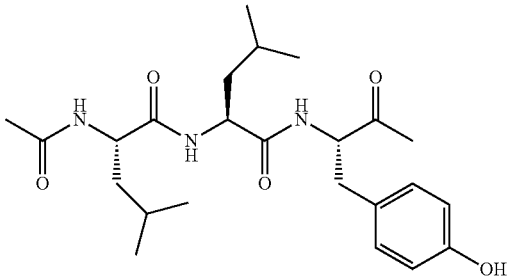

[4] A compound of the following formula (3) or a salt thereof.

(3)

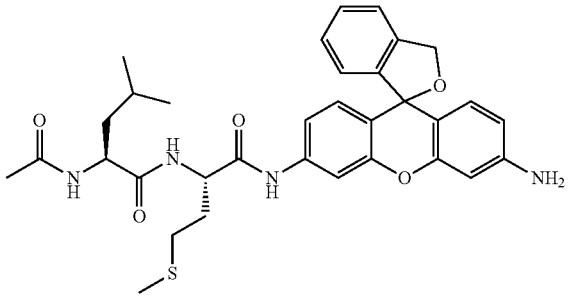

[5] A compound of the following formula (4) or a salt thereof.

(4)

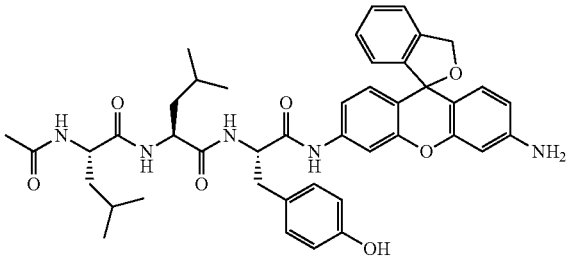

[6] A fluorescent probe containing a compound according so to any of [1]-[5] or a salt thereof.

[7] A method for measuring calpain, comprising the following steps: (a) a step for bringing a compound according to any of [1]-[5] or a salt thereof and calpain into contact and (b) a step for measuring the fluorescence intensity of the compound produced in step (a) after contact with calpain.

[8] A diagnostic for retinal disease containing a compound according to any of [1]-[5] or a salt thereof.

[9] The diagnostic according to [8], wherein the retinal disease is glaucoma, retinitis pigmentosa, age-related macular degeneration, or retinal neuropathy or retinal vascular occlusive disease associated with diabetes.

[10] The diagnostic according to [9] wherein the glaucoma is normotensive glaucoma.

Advantages of the Invention

The use of the compound of the present invention makes it possible to provide a bright flourescent probe that can detect calpain activity in the green wavelength region, has excellent photostability, and a high quantum yield of the fluorescent substance generated by reaction with calpain.

The use of the compound of the present invention also makes it possible to provide a diagnostic of retinal diseases that permits real time monitoring of calpain activity in live cells, clarification of pathology, clinical diagnosis, and assessment of therapeutic effect in retinal diseases that progress via activation of calpain in the field of ophthalmology (for example, glaucoma, retinitis pigmentosa, age-related macular degeneration, retinal neuropathy or retinal vascular occlusive disease associated with diabetes, and other such retinal diseases). In particular, because it emits green fluorescence of basically the same wavelength as fluorescein, the compound of the present invention can be observed by a fluorescein fluorescence fundus angiograph, which is already widely used in the field of ophthalmology, and is immediately applicable to actual clinical practice.

Therefore, the present invention contributes to clarifying the pathology of retinal neuropathy that progresses via activation of calpain in the field of ophthalmology as a tool for monitoring calpain activity in live cells.

BEST MODE FOR CARRYING OUT THE INVENTION

Figure 1A:
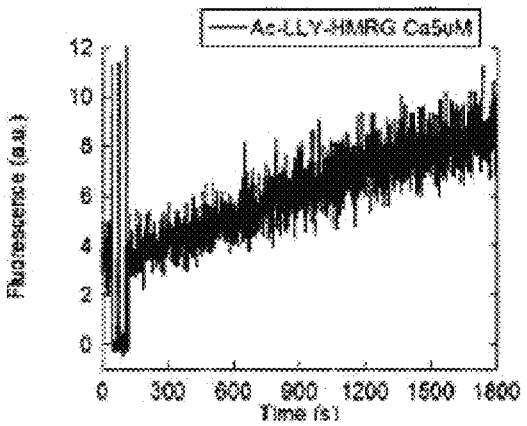
FIG. 1a shows the changes in the absorption and fluorescence spectra of Ac-LLY-HMRG due to calpain addition (using calpain 1)

In the present specification, an alkyl group may be any alkyl group comprising linear, branched, cyclic, or a combination thereof. The number of carbon atoms in the alkyl group is not particularly restricted; for example, about 1-6 carbon atoms or about 1-4 carbon atoms. In this specification, alkyl groups may have one or more optional substituents. Examples of substituents include, but are not limited to, an alkoxy group, halogen atom (may be any of a fluorine atom, chlorine atom, bromine atom, or iodine atom), amino group, mono- or di-substituted amino group, substituted silyl group, acyl group, or the like. When an alkyl group has two or more substituents, they may be the same or different. The same is also true for alkyl moieties of other substituents that include an alkyl moiety (for example, an alkyloxy group, aralkyl group, or the like).

In addition, in the present specification, an aryl group may be either a monocyclic aryl group or a fused polycyclic aryl group, and may include one or more heteroatoms (for example, an oxygen atom, nitrogen atom, sulfur atom, or the like) as ring members. In the present specification, an aryl group may have one or more optional substituents on its ring. Examples of substituents include, but are not limited to, an alkoxy group, halogen atom, amino group, mono- or di-substituted amino group, substituted silyl group, acyl group, or the like. When an aryl group has two or more substituents, they may be the same or different. The same is also true for aryl moieties of other substituents that include an aryl moiety (for example, an aryloxy group, aralkyl group, or the like).

One embodiment of the present invention is a compound of the following general formula (I):

[Chemical formula 1]

(I)

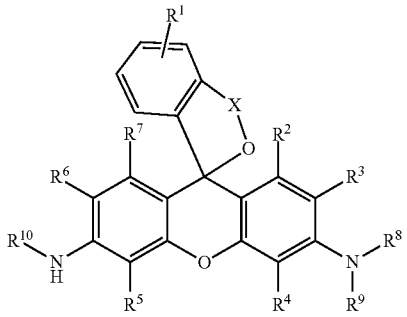

wherein, $R^1$ is a hydrogen atom or from one to four of the same or different substituents that bond to the benzene ring;

$R^2$, $R^3$, $R^4$, $R^5$, $R^6$, and $R^7$ are, each independently, a hydrogen atom, hydroxyl group, alkyl group, or halogen atom;

$R^8$ and $R^9$ are, each independently, a hydrogen atom or alkyl group;

X is a $C_1$-$C_3$ alkylene group;

$R^{10}$ represents a monovalent substituent cleaved by contact with calpain;

or a salt thereof.

$R^1$ represents a hydrogen atom or from one to four substituents that bond to the benzene ring. Examples of substituents include, but are not limited to, an alkyl group, alkoxy group, halogen atom, amino group, mono- or disubstituted amino group, substituted silyl group, acyl group, or the like. When there are two or more substituents on the benzene ring, they may be the same or different. A hydrogen atom is preferred as $R^1$.

$R^2$, $R^3$, $R^4$, $R^5$, $R^6$, and $R^7$ each independently represent a hydrogen atom, hydroxyl group, alkyl group, or halogen atom. $R^2$ and $R^7$ are preferably hydrogen atoms. $R^3$, $R^4$, $R^5$, and $R^6$ are also preferably hydrogen atoms. It is more preferred that $R^2$, $R^3$, $R^4$, $R^5$, $R^6$, and $R^7$ are all hydrogen atoms.

$R^8$ and $R^9$ each independently represent a hydrogen atom or alkyl group. When $R^8$ and $R^9$ both represent alkyl groups, they may be the same or different. For example, it is preferred when $R^8$ and $R^9$ are both hydrogen atoms or when $R^8$ is an alkyl group and $R^9$ is a hydrogen atom. It is more preferred that $R^8$ and $R^9$ are both hydrogen atoms.

X represents a $C_1$-$C_3$ alkylene group. An alkylene group may be a linear alkylene group or a branched alkylene group. For example, in addition to a methylene group (—$CH_2$—), ethylene group (—$CH_2$—$CH_2$—), propylene group (—$CH_2$—$CH_2$—$CH_2$—), —$CH(CH_3)$—, —$CH_2$—$CH(CH_3)$—, —$CH(CH_2CH_3)$—, and the like can also be used as branched alkylene groups. Among these, a methylene group or ethylene group is preferred, and a methylene group is more preferred.

In general formula (I), $R^{10}$ represents a monovalent substituent that is cleaved by contact with calpain. A monovalent substituent including an oligopeptide residue is preferred as the monovalent substituent that is cleaved by contact with calpain.

Monovalent substituents including an oligopeptide residue having a sequence of Leu-Leu-Tyr, Leu-Met, Leu-Leu-Val-Tyr, Thr-Pro-Leu-Leu, Thr-Pro-Leu-Lys, Thr-Pro-Leu-Phe, and Leu-Try (the amino acid at the right end of the sequence bonds directly to the NH group bonded to the xanthene skeleton) are preferred as monovalent substituents including an oligopeptide residue.

The N end of the monovalent substituent including an oligopeptide residue may be protected. Examples of protecting groups include an acetyl group, glutaryl group, succinyl group, tert-butoxycarbonyl group, benzyloxycarbonyl group, and the like, but substituents other than these may be used.

In one embodiment of the present invention, the monovalent substituent including an oligopeptide residue is represented by the following formula (1) or (2).

(1)

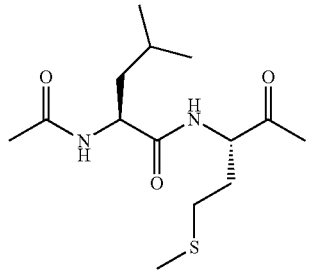

(2)

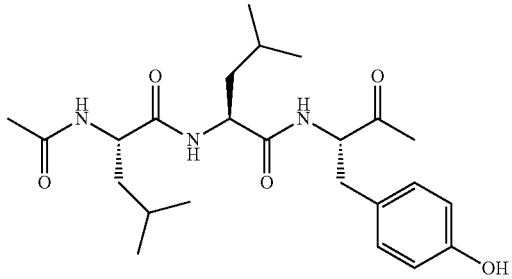

One preferred embodiment of the present invention is a compound represented by the following formula (3) or (4), or a salt thereof.

(3)

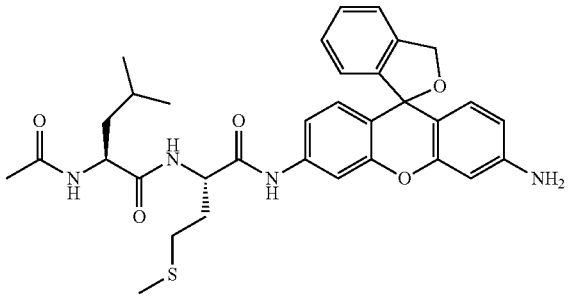

-continued (4)

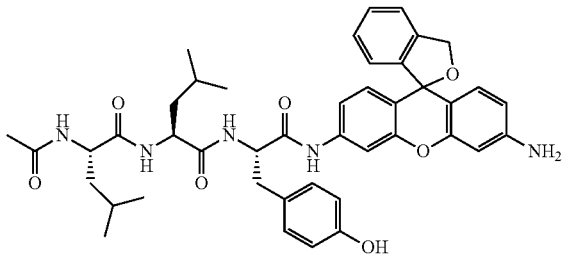

Examples of salts of compounds represented by general formula (I) and formulas (3) and (4) in the present invention include base addition salts, acid addition salts, amino acid salts, and the like. Examples of base addition salts include metal salts such as a sodium salt, potassium salt, calcium salt, magnesium salt, or the like, an ammonium salt, or an organic amine salt such as a triethylamine salt, piperidine salt, morpholine salt, or the like. Examples of acid addition salts include mineral acid salts such as a hydrochloride, sulfate, nitrate, and the like, and organic acid salts such as a methanesulfonate, p-toluenesulfonate, citrate, oxalate, and the like. Examples of amino acid salts include a glycine salt and the like. However, salts of compounds of the present invention are not limited to these.

Compounds represented by general formula (I) sometimes have one or more asymmetrical carbons in accordance with the types of substituents and can exist as stereoisomers such as optical isomers and diastereomers. Stereoisomers of a pure form, any mixtures of stereoisomers, racemic mixtures, and the like are all encompassed within the scope of the present invention. In addition, compounds represented by general formula (I) or salts thereof can also exist as hydrates or solvates. All of these are encompassed within the scope of the present invention. The type of solvent that forms a solvate is not particularly restricted; examples include ethanol, acetone, isopropanol, and other such solvents.

A fluorescent probe including a compound represented by general formula (I), formula (3), or formula (4) or a salt thereof provided by the present invention can generate a compound in which the absorption wavelength is shifted to a longer wavelength (corresponding to a compound in which $R^{10}$ in the above general formula (I) is a hydrogen atom) by cleaving the $R^{10}$ substituent or the monovalent substituent including an oligopeptide residue by contact with calpain, and can be used suitably as a fluorescent probe for measuring calpain.

Calpain can be measured using the above fluorescent probe in accordance with methods known to those skilled in the art. The fluorescent probe can therefore also be used as a reagent for research and also as a reagent for diagnosis of humans and animals. For example, using the above fluorescent probe makes it possible to measure the concentration and amount of a substance to be measured in a test tube. Alternatively, measurement is possible by causing the fluorescent probe to be taken up within living cells or a living body and imaging by a bioimaging technique. A typical example is a method that includes the following steps: (a) a step for bringing a compound represented by general formula (I) having a monovalent substituent that is cleaved by contact with calpain or a salt thereof and calpain into contact and (b) a step for measuring the fluorescence intensity of the compound produced in step (a) after contact with calpain.

The method for using the fluorescent probe of the present invention is not particularly restricted. Examples include measurement of the activity of isolated, purified enzymes and calpain included in cell lysate, measurement of calpain activity in living cells, measurement of the activity of enzymes that serve as a cancer biomarker in living tissues making use of the long wavelength optical property, and the like.

Another embodiment of the present invention is a diagnostic for retinal diseases including a compound and salt of the present invention.

Another embodiment of the present invention is a diagnostic for retinal neuropathy that progresses via activation of calpain in the field of ophthalmology including a compound and salt of the present invention.

Yet another embodiment of the present invention is a diagnostic for glaucoma, retinitis pigmentosa, age-related macular degeneration, retinal neuropathy or retinal vascular occlusive disease associated with diabetes (retinal vein occlusion or retinal artery occlusion) including a compound and salt of the present invention.

Yet another embodiment of the present invention is a diagnostic for glaucoma including a compound and salt of the present invention.

Yet another aspect of the present invention is a diagnostic for normotensive glaucoma including a compound and salt of the present invention.

Compounds and salts of the present invention can detect calpain activity in the green wavelength region and have excellent photostability. Their use in the field of ophthalmology therefore permits clarification of the pathology, clinical diagnosis, and assessment of the therapeutic effect in retinal neuropathy that progresses via activation of calpain, for example, glaucoma (especially normotensive glaucoma), retinitis pigmentosa, age-related macular degeneration, retinal neuropathy and retinal vascular occlusive diseases associated with diabetes, and other such retinal diseases.

In addition, since compounds of the present invention emit a green fluorescence of basically the same wavelength as fluorescein, compounds of the present invention can be observed by a fluorescein fluorescence fundus angiograph, which is already widely used in the field of ophthalmology, and are immediately applicable to actual clinical practice.

EXAMPLES

The present invention is explained more concretely below through examples. The scope of the present invention, however, is not limited to the following examples.

Synthesis Example 1

Compound 1 (Ac-LLY-HMRG) of the present invention was synthesized according tyo the following scheme 1.

Scheme 1: Method for synthesizing compound 1 (Ac-LLY-HMRG) of the present invention

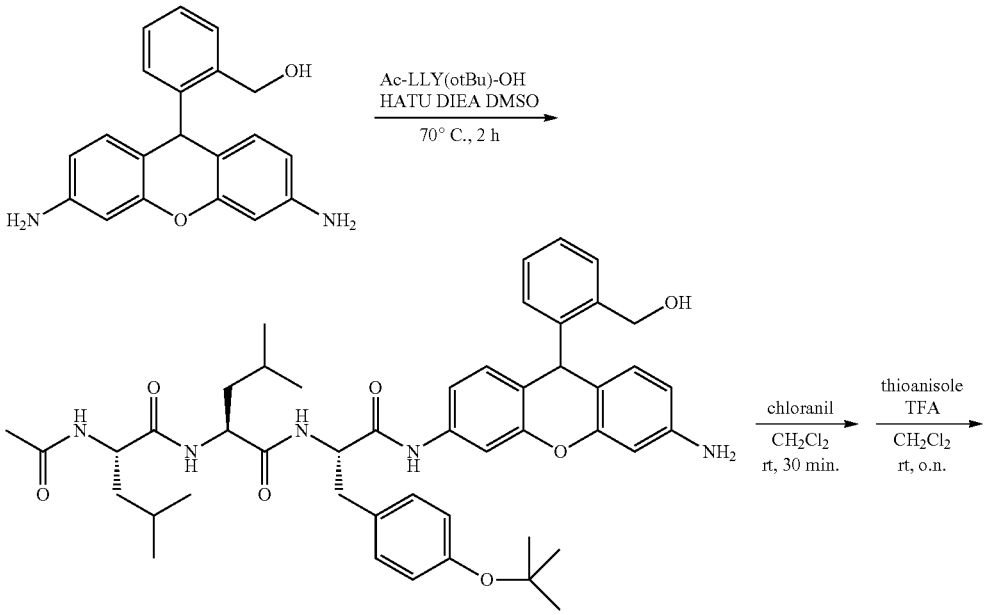

Ac-LLY(otBu)-leuco-HMRG

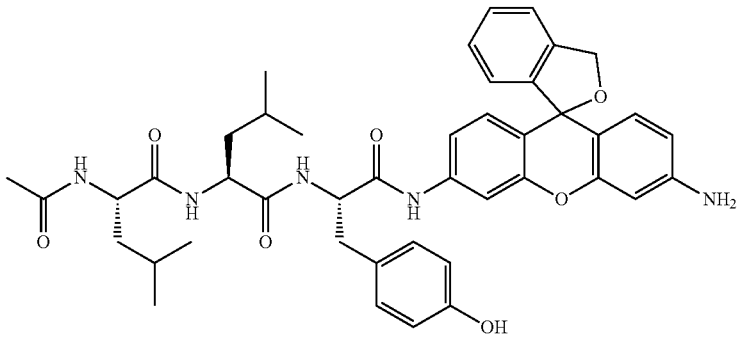

Ac-LLY-HMRG (1) Synthesis of Leuco-HMRG

Three hundred sixty-two grams (0.986 mmol, 1 Eq) of Rhodamin 110 and 400 μL (7.504 mmol, 7.6 Eq) of sulfuric acid were dissolved in 40 mL of methanol and stirred overnight at 80° C. The reaction solvent was removed under reduced pressure, and the product was neutralized by sodium bicarbonate aqueous solution. The solid obtained was extracted by water and methanol. The solvent of the organic layer was removed, and a solid was obtained. The solid was then dissolved in 60 mL of THF, 247.8 mg (6.53 mmol, 6.6 Eq) of LAH was added while cooling by ice, and the solution was stirred overnight at 0° C. in an argon atmosphere. After quenching by methanol, 50 mL of dichloromethane and 100 mL of Rochelle salt aqueous solution were added and stirred overnight. Water was added to the reaction mixture, which was then extracted by dichloroethane and washed with brine. Sodium sulfate was added to the organic layer, the solvent was removed after filtration, and a solid was obtained. The solid was purified by silica gel chromatography (dichloromethane/methanol=97/3), and the target compound (64 mg, 21%) was obtained.

$^1$H NMR (400 MHz, DMSO): δ 7.36-7.34 (m, 1H), 7.12-7.10 (m, 2H), 6.96-6.94 (m, 1H), 6.59 (d, 2H, J=8.2 Hz), 6.24 (d, 2H, J=2.2 Hz), 6.16 (dd, 2H, J=8.2 Hz, 2.2 Hz), 5.29 (s, 1H), 5.19 (t, 1H, J=4.9 Hz), 5.07 (s, 4H), 4.54 (d, 2H, J=4.9 Hz). The HRMS (ESI$^+$) was calculated for $[M+Na]^+$ as 341.12605; The value found was 341.12576 (−0.29 mmu).

(2) Synthesis of Ac-LLY-HMRG (Compound 1 of the Present Invention)

A quantity of 6.3 mg (0.0198 mmol, 2 Eq) of leuco-HMRG was dissolved in 0.2 mL of dimethylsulfoxide (DMSO), 5 mg (0.0099 mmol, 1 Eq) of Ac-Leu-Leu-Tyr (OtBu)-OH, 5.7 mg (0.0150 mmol, 1.5 Eq) of O-(benzotriazol-1-yl)-N,N,N',N'-tetramethyluronium hexafluorophosphate (HATU), and 5 μL (0.0287 mmol, 2.9 Eq) of N,N-diisopropylethylamine (DIEA) were added, and stirred for two hours at 70° C. in an argon atmosphere. Water was added to the reaction mixture, which was extracted by ethyl acetate and washed with brine. After drying the organic layer by sodium sulfate, the solvent was evaporated under reduced pressure. A quantity of 8.0 mg (0.0099 mmol, 1 Eq) of the residue and 6.6 mg (0.0268 mmol, 2.7 Eq) of chloranil were dissolved in dichloromethane solution and stirred for 30 minutes at room temperature. A quantity of 58 μL (0.495 mmol, 50 Eq) of thioanisole and 2 mL of trifluoroacetic acid (TFA) were then added, stirred for seven hours, and crudely purified by a short column. Next, purification was performed by HPLC (eluent A (99% $H_2O$ (0.1% TFA)/1% $CH_3CN$) and eluent B (99% $CH_3CN$, 1% $H_2O$) (A/B=90/10 to 10/90, 20 min)), and the target compound (1.4 mg, 19% (in two steps)) was obtained.

The HRMS ($ESI^+$) was calculated for $[M+H]^+$ as 748.37048; The value found was 748.36998 (−0.5 mmu).

Synthesis Example 2

Compound 2 (Ac-LM-HMRG) of the present invention was synthesized according to the following scheme 2.

Scheme 2: Method for synthesizing compound 2 (Ac-LM-HMRG) of the present invention

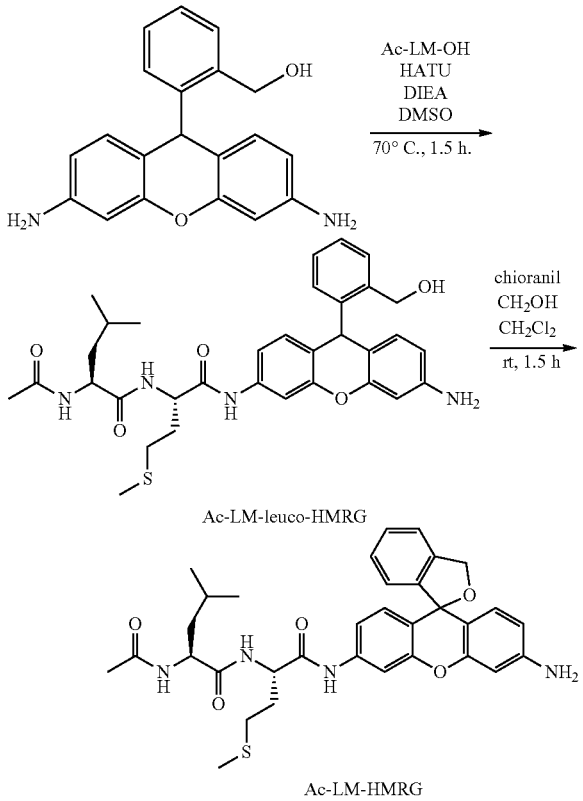

(1) Synthesis of Ac-LM-Leuco-HMRG

A quantity of 10.6 mg (0.033 mmol, 12 Eq) of leuco-HMRG was dissolved in 0.3 mL of dimethylsulfoxide (DMSO), 5 mg (0.016 mmol, 1 Eq) of Ac-Leu-Met-OH, 9.5 mg (0.025 mmol, 1.5 Eq) of O-(benzotriazol-1-yl)-N,N,N',N'-tetramethyluronium hexafluorophosphate (HATU), and 8.6 μL (0.049 mmol, 3 Eq) of N,N-diisopropylethylamine (DIEA) were added, and stirred for 90 minutes at 70° C. in an argon atmosphere. Water was added to the reaction mixture, which was extracted by ethyl acetate and washed with brine. After drying the organic layer by sodium sulfate, the solvent was evaporated under reduced pressure. The residue was purified by silica gel chromatography (dichloromethane/methanol=91/9), and the target compound (8.1 mg, 82%) was obtained.

The HRMS ($ESI^+$) was calculated for $[M+Na]^+$ as 627.26116; The value found was, 627.25978 (−1.4 mmu).

(2) Synthesis of Ac-LM-HMRG (Compound 2 of the Present Invention

A quantity of 8.1 mg (0.0134 mmol, 1 Eq) of Ac-LM-leuco-HMRG and 9.2 mg (0.0374 mmol, 2.8 Eq) of chloranil were dissolved in dichloromethane solution and stirred for 30 minutes at room temperature. After crude purification by a short column, purification was conducted using HPLC (eluent A (99% $H_2O$ (0.1% TFA)/1% $CH_3CN$) and eluent B (99% $CH_3CN$, 1% $H_2O$) (A/B=75/25 to 25/75, 30 min)), and the target compound (1.3 mg, 13% (in two steps)) was obtained.

The HRMS ($ESI^+$) was calculated for $[M+H]^+$ as 603.26357 The value found was 603.26343 (−0.13 mmu).

Reaction Mechanism of Calpain Probes (Ac-LLY-HMRG, Ac-LM-HMRG)

Probes (Ac-LLY-HMRG, Ac-LM-HMRG) in which an amino acid that is a substrate of calpain is connected by an amide bond to an amino group of the xanthene ring of HMRG are converted to HMRG when the amino acid is cut out by calpain. Such a change from a closed-ring structure to an open-ring structure after the reaction causes a significant change from no absorption/no fluorescence to strong fluorescence (scheme 3).

Scheme 3: Reaction scheme of calpain probes with calpin

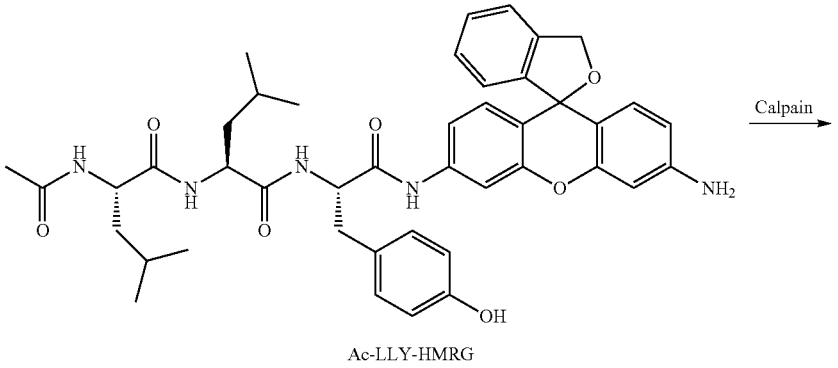

-continued

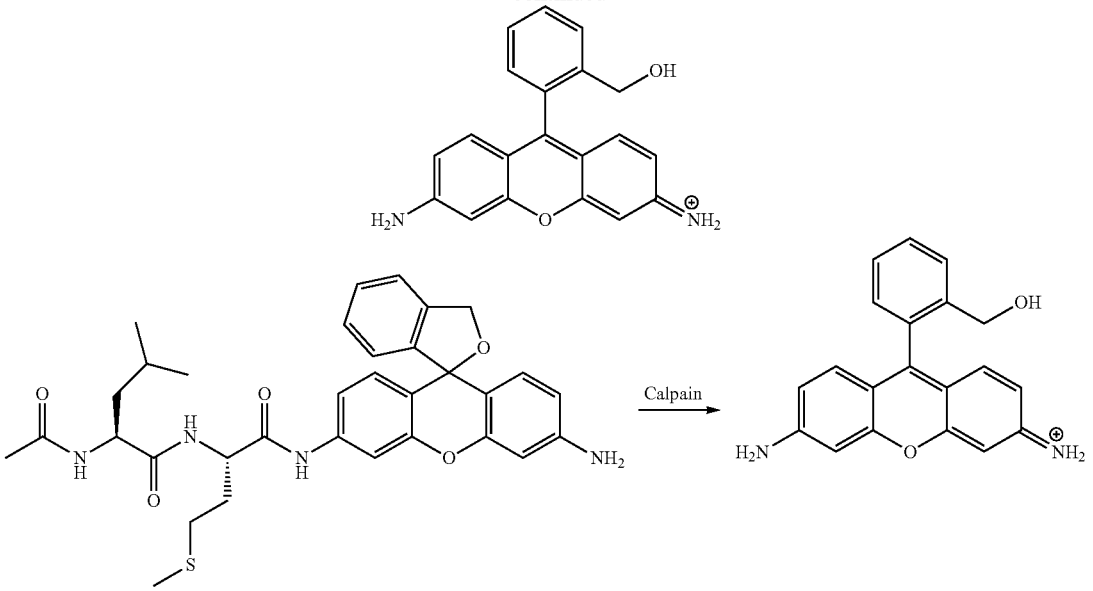

Example 1

Measurement of the Optical Properties of Ac-LLY-HMRG and Ac-LM-HMRG

The optochemical properties of Ac-LLY-HMRG and Ac-LM-HMRG were measured in 0.2 M sodium phosphate buffer of pH 2. Table 1 below also shows the optochemical properties of HMRG, which is the enzymatic reaction product.

TABLE 1

| | $Abs_{max}$ [nm] | $Em_{max}$ [nm] | $\Phi_n$ |
|---|---|---|---|
| Ac-LLY-HMRG | 470 | 526 | 0.19 |
| Ac-LM-HMRG | 470 | 529 | 0.32 |
| HMRG | 501 | 524 | 0.81 |

Example 2

Evaluation of Ac-LLY-HMRG as a Fluorescent Probe (In Vitro Enzyme Assay Using Calpain)

Figure 1B:
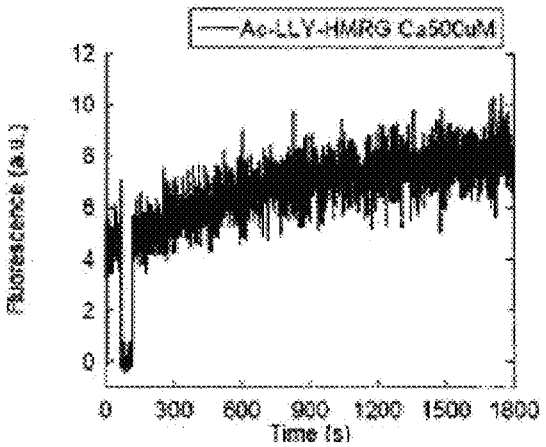
FIG. 1b shows the changes in the absorption and fluorescence spectra of Ac-LLY-HMRG due to calpain addition (using calpain 2)

A calpain enzyme addition assay was conducted in Tris buffer under the following conditions using a probe synthesized and designed by the above method. As a result, the absorption and fluorescence intensity of Ac-LLY-HMRG increased about two-fold due to the enzymatic reaction, and it was confirmed to function as a calpain probe. The results are shown in FIG. 1a (using calpain 1) and FIG. 1b (using calpain 2).

(Experimental Conditions)

A quantity of 3 μL of a DMSO solution (1 mM) of the probe was dissolved in 3 mL of 50 mM Tris buffer (pH 7.4) (containing 5 μM of $CaCl_2$) for calpain 1 and 500 μM of $CaCl_2$ for calpain 2) (final probe concentration: 1 μM). Calpain (2.4 units of calpain 1 and 3.8 units of calpain 2) was added, and an enzymatic reaction was conducted at 25° C. The excitation wavelength was 495 nm, and the fluorescence wavelength was 524 nm.

(Enzymes)

Calpain 1: calpain-1 from human erythrocytes (Cat. No. 208713)

Calpain 2: calpain-2 from porcine kidney (Cat. No. 208715)

Example 3

Evaluation of Ac-LM-HMRG as a Fluorescent Probe (In Vitro Enzyme Assay Using Calpain)

Figure 2A:
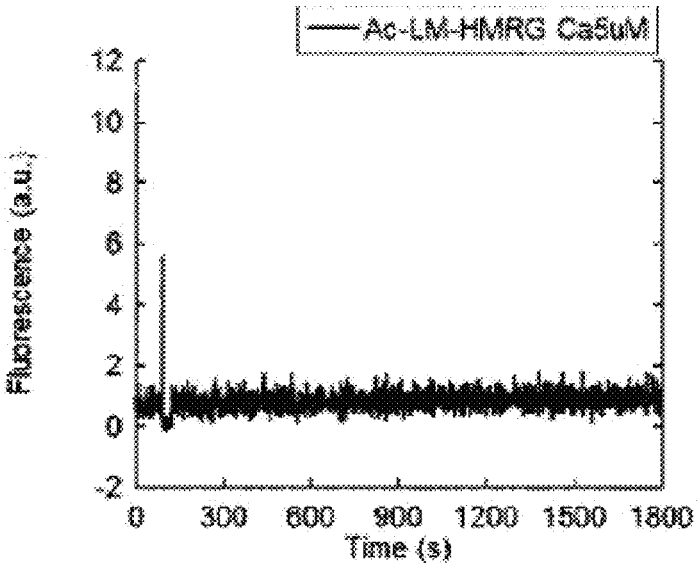
FIG. 2a shows the changes in the absorption and fluorescence spectra of Ac-LM-HMRG due to calpain addition (using calpain 1)
Figure 2B:
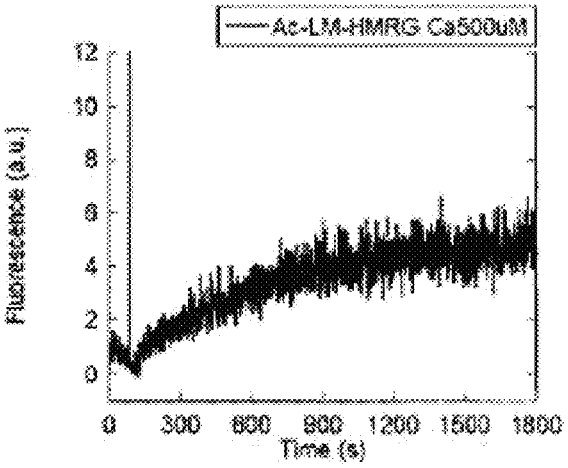
FIG. 2b shows the changes in the absorption and fluorescence spectra of Ac-LM-HMRG due to calpain addition (using calpain 2)

A calpain enzyme addition assay was conducted in Tris buffer using a probe synthesized and designed by the above method. As a result, the absorption and fluorescence intensity of Ac-LM-HMRG increased about four-fold due to the enzymatic reaction with calpain 2, and it was confirmed to function as a calpain probe. The results are shown in FIG. 2a (using calpain 1) and FIG. 2b (using calpain 2).

(Experimental Conditions)

A quantity of 3 μL of a DMSO solution (1 mM) of the probe was dissolved in 3 mL of 50 mM Tris buffer (pH 7.4) (containing 5 μM of $CaCl_2$) for calpain 1 and 500 μM of $CaCl_2$ for calpain 2) (final probe concentration: 1 μM). Calpain (24 units of calpain 1 and 38 units of calpain 2) was added, and an enzymatic reaction was conducted at 25° C. The excitation wavelength was 495 nm, and the fluorescence wavelength was 524 nm.

(Enzymes)

Calpain 1: calpain-1 from human erythrocytes (Cat. No. 208713)

Calpain 2: calpain-2 from porcine kidney (Cat. No. 208715)

Example 4

Live Cell Imaging Using Ac-LLY-HMRG

The calpain activity in HeLa cells was visualized by the following procedure using Ac-LLY-HMRG.

(Experimental Procedure)

(a) HeLa cells were incubated for one hour at 37° C. using FBS (BD Pharmingen stain buffer)-free DMEM (Dulbecco's modified Eagle's medium), and also incubated for 30 minutes by 10 μM of Ac-LLY-HMRG. Fluorescence images and transmission images were taken thereafter using a confocal microscope.

Figure 3:
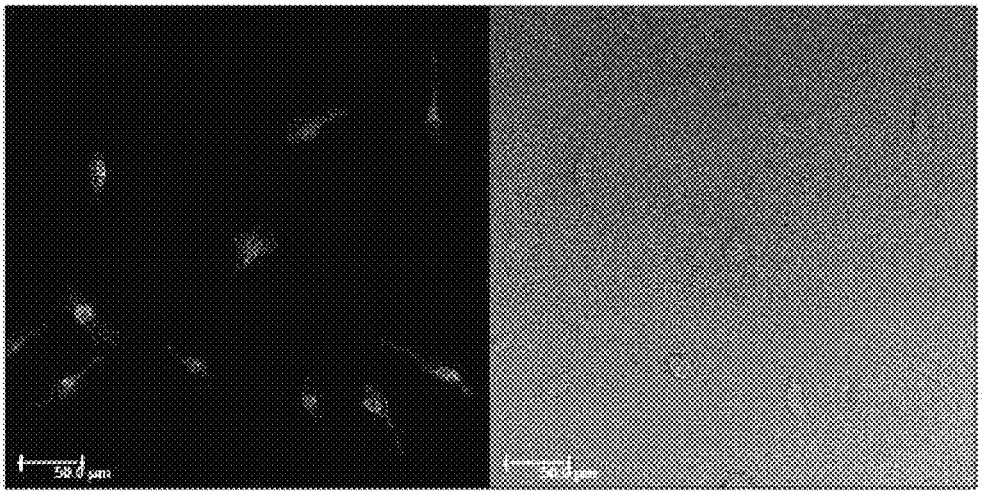
FIG. 3 shows live cell imaging using Ac-LLY-HMRG

The results are shown in FIG. 3 (the left side of FIG. 3 is the fluorescence image; the right side is the transmission image). The scale bar in the drawing is 50 μm.

As shown in FIG. 3, addition of Ac-LLY-HMRG made it possible to monitor the calpain activity inside HeLa cells.

Example 5

Live Cell Imaging Using Ac-LM-HMRG

The calpain activity in HeLa cells was visualized by the following procedure using Ac-LM-HMRG.

(Experimental Procedure)

(a) HeLa cells were incubated for one hour at 37° C. using FBS (BD Pharmingen stain buffer)-free DMEM (Dulbecco's modified Eagle's medium), (b) 1 μM ALLN (calpain selective inhibitor)-containing DMEM (FBS (−)), (c) 2 μM ALLN-containing DMEM (FBS (−)), and (d) 5 μM ALLN-containing DMEM (FBS (−)), and also incubated for 30 minutes by 10 μM of Ac-LM-HMRG. Fluorescence images and transmission images were taken thereafter using a confocal microscope. The results are shown in FIGS. 4a-4d (the left side of each drawing is the fluorescence image; the right side is the transmission image). The scale bar in the drawing is 50 μm.

Figure 4A:
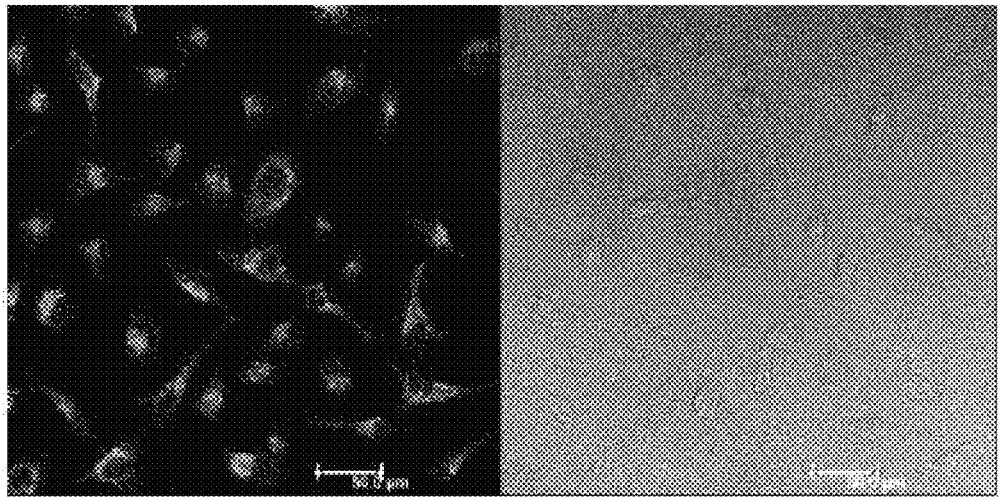
FIG. 4a shows live cell imaging using Ac-LM-HMRG (no ALLN added)
Figure 4B:
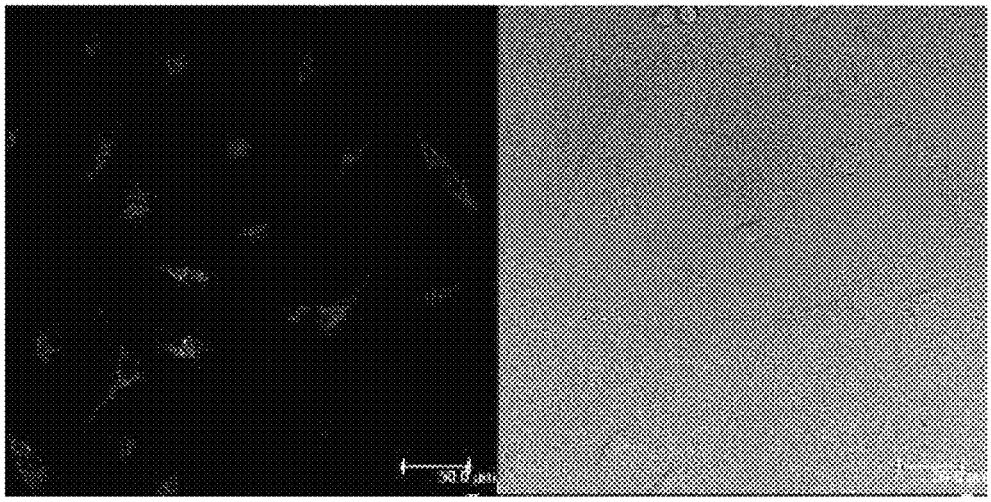
FIG. 4b shows live cell imaging using Ac-LM-HMRG (1 μM of ALLN added)
Figure 4C:
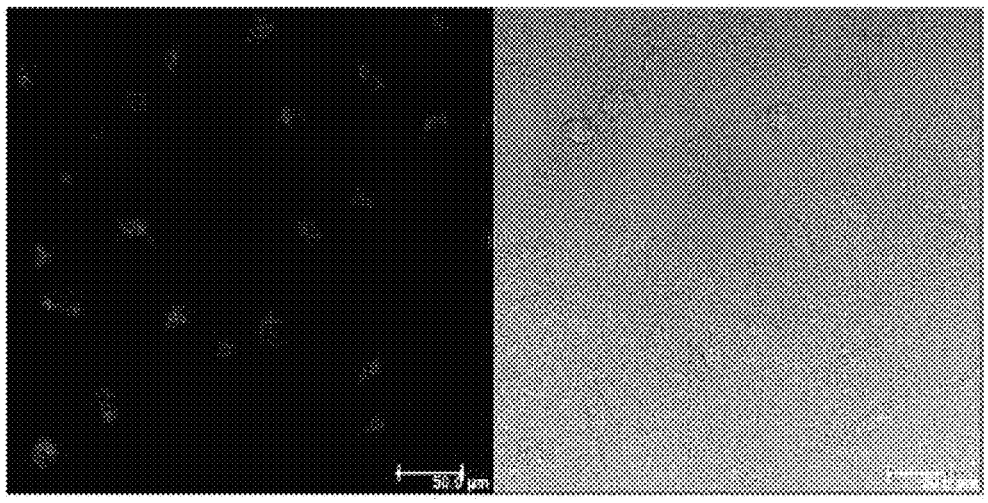
FIG. 4c shows live cell imaging using Ac-LM-HMRG (2 μM of ALLN added)
Figure 4D:
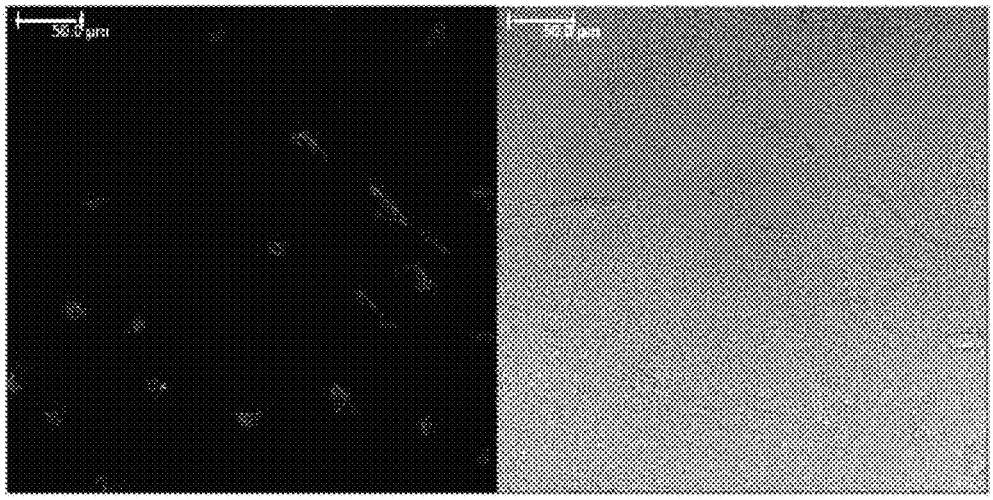
FIG. 4d shows live cell imaging using Ac-LM-HMRG (5 μM of ALLN added)

As shown in FIG. 4a, addition of Ac-LM-HMRG made it possible to monitor the calpain activity inside HeLa cells. Also, as shown in FIGS. 4b-4d, addition of ALLN, which is a calpain selective inhibitor, decreased the fluorescence intensity within the cells, and the fluorescence intensity decreased as the added concentration of ALLN increased.

As illustrated in the above examples, the present invention makes it possible to provide new fluorescent probes having calpain as the target. Specifically, as shown in Examples 2 and 3, Ac-LLY-HMRG and Ac-LM-HMRG were demonstrated to increase in fluorescence intensity due to reaction with calpain. Ac-LLY-HMRG and Ac-LM-HMRG both also presented an increase in fluorescence intensity when applied to cells. The fact that the increase in the fluorescence of Ac-LM-HMRG decreased in the inhibitor addition study of Example 5 also showed that Ac-LM-HMRG permits the specific fluorescent detection of intracellular calpain activity.

Example 6

Evaluation of Ac-LM-HMRG Using a Rat NMDA Injury Model (Experimental Procedure)

SD rats were placed under general anesthesia using Nembutal. N-methyl-D-aspartic acid (NMDA) (10 mM, 2 μL) or PBS was administered to the eye. The animals were again placed under anesthesia by ketamine-xylazine mixture four hours later, and Ac-LM-HMRG (2 mM, 2 μL) was administered to the eye. The fundus was photographed by an F10 (Nidec confocal biomicroscope).

The results are shown in FIGS. 5a-5d and FIGS. 6a-6d. In FIGS. 5 and 6, locations indicated by an arrow show nerve cells stained by HMRG.

Figure 5A:
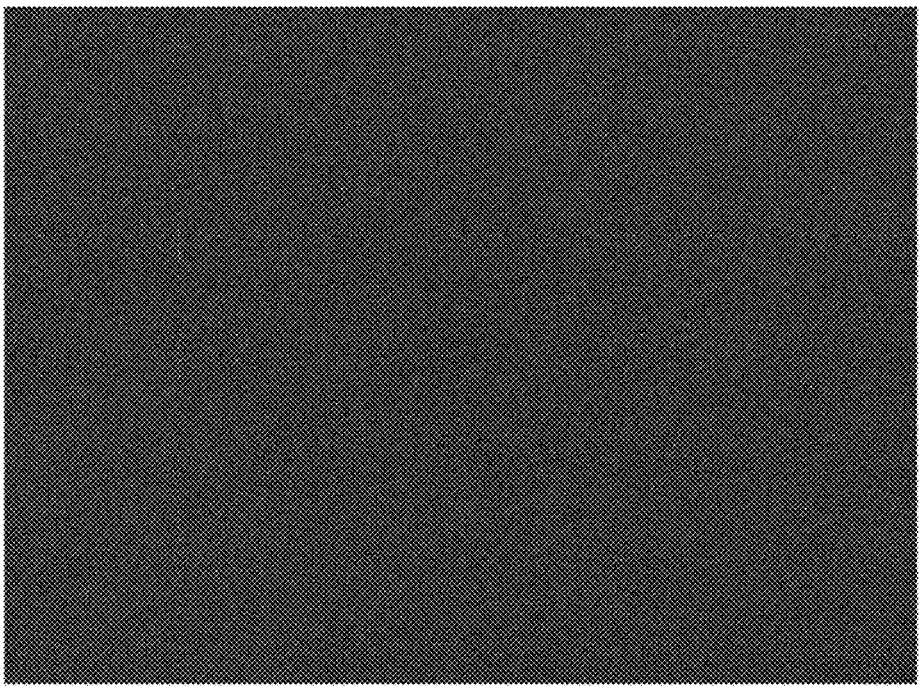
FIG. 5a is a fundus photograph of before Ac-LM-HMRG administration in the NMDA group
Figure 5B:
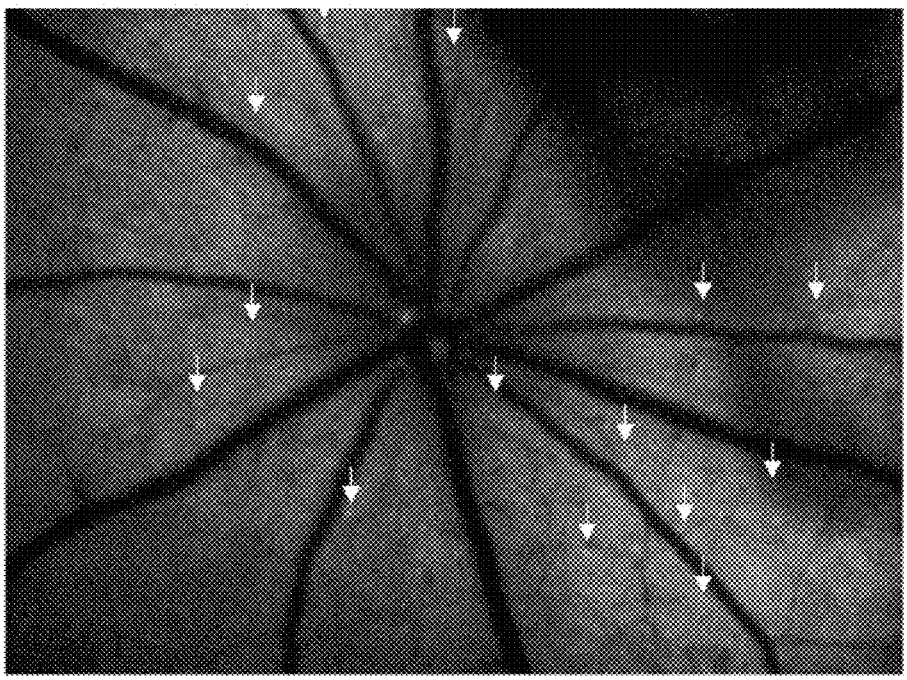
FIG. 5b is a fundus photograph of 30 minutes after Ac-LM-HMRG administration in the NMDA group
Figure 5C:
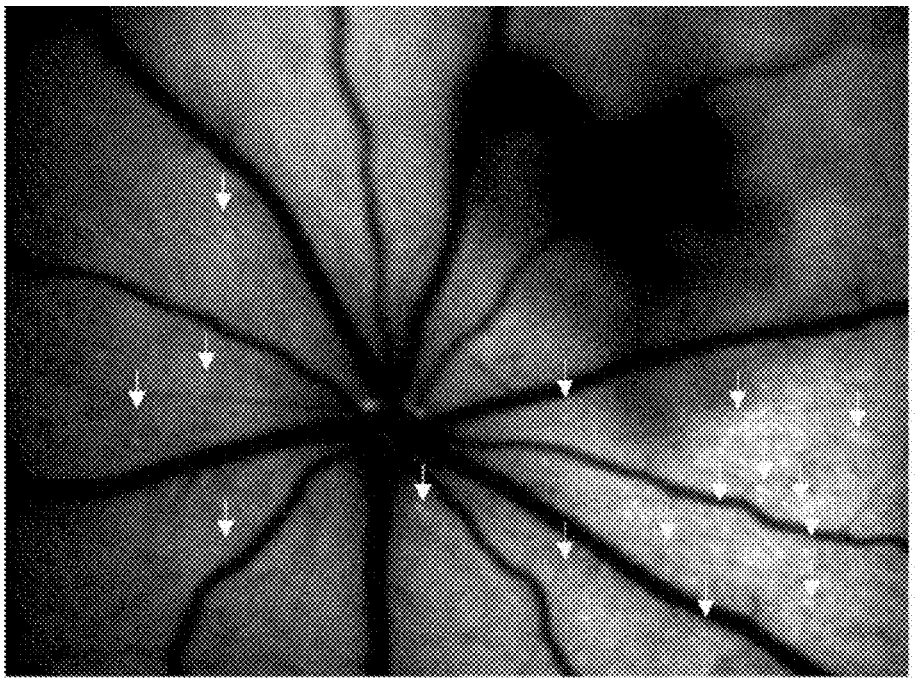
FIG. 5c is a fundus photograph of 60 minutes after Ac-LM-HMRG administration in the NMDA group
Figure 5D:
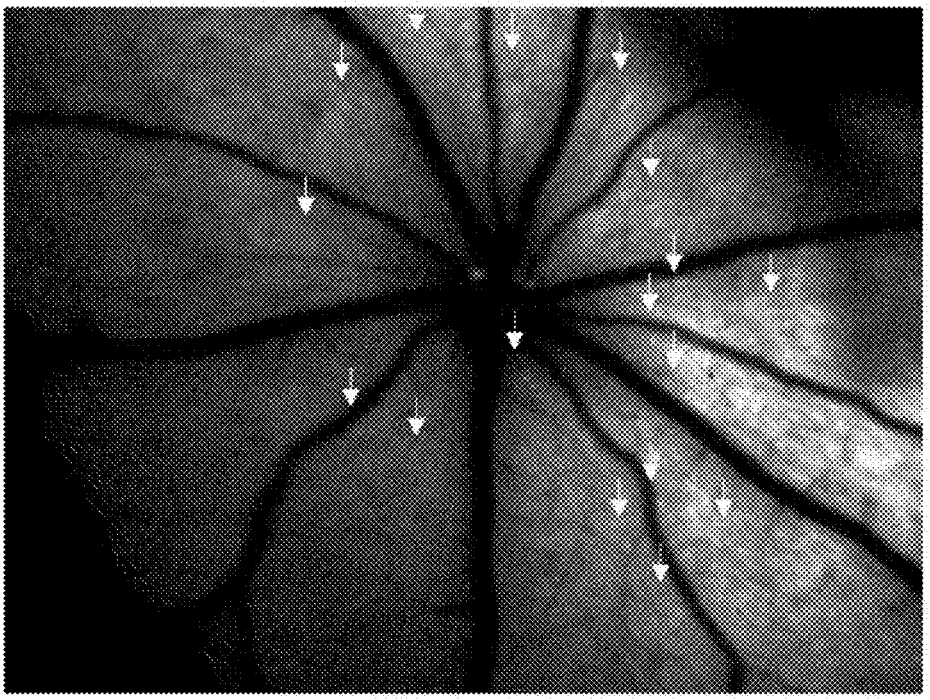
FIG. 5d is a fundus photograph of 90 minutes after Ac-LM-HMRG administration in the NMDA group
Figure 6A:
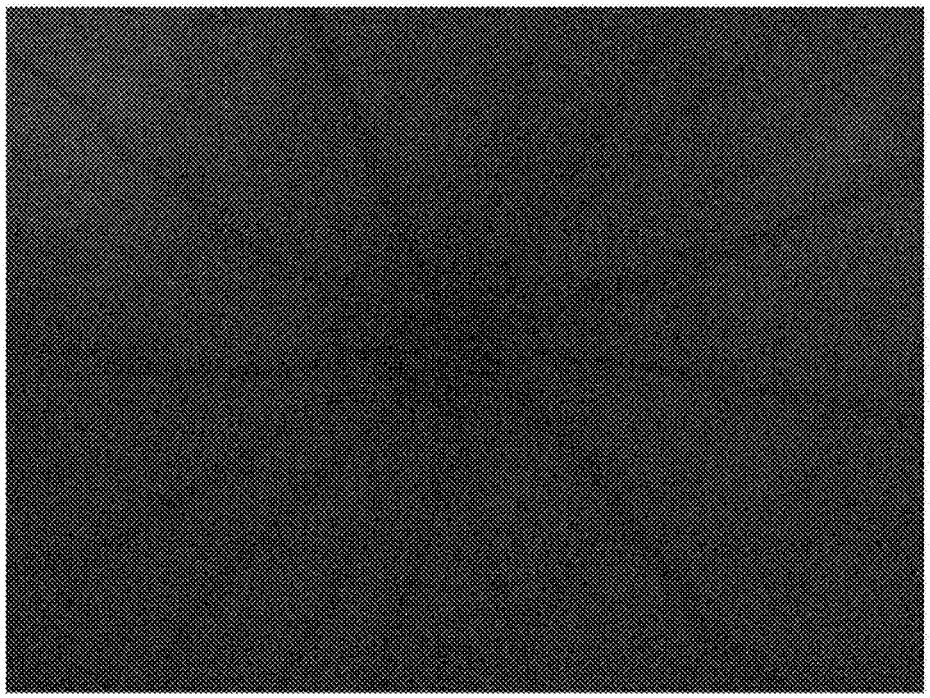
FIG. 6a is a fundus photograph of before Ac-LM-HMRG administration in the PBS group
Figure 6B:
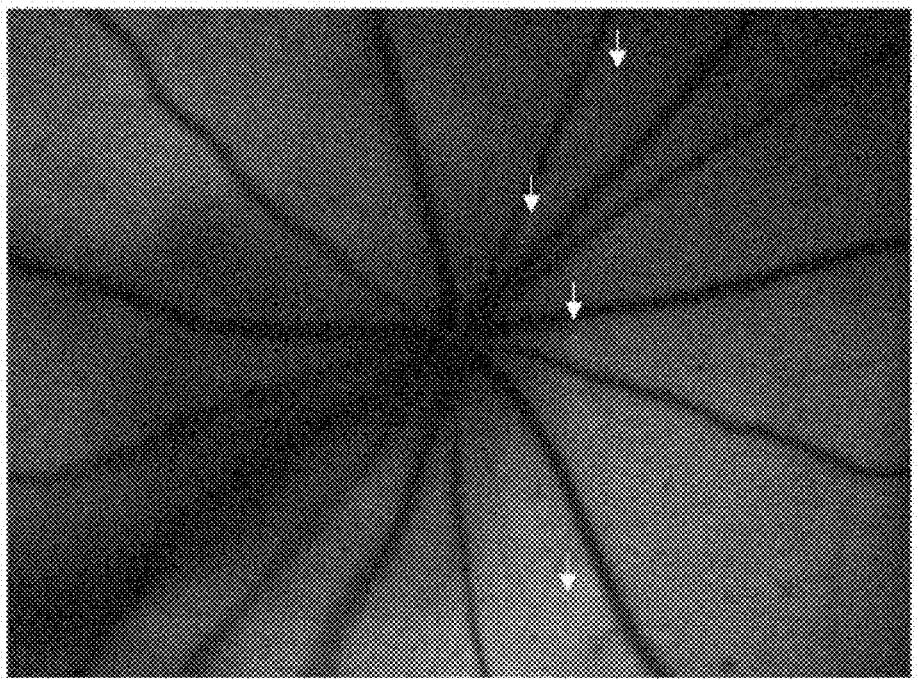
FIG. 6b is a fundus photograph of 30 minutes after Ac-LM-HMRG administration in the PBS group
Figure 6C:
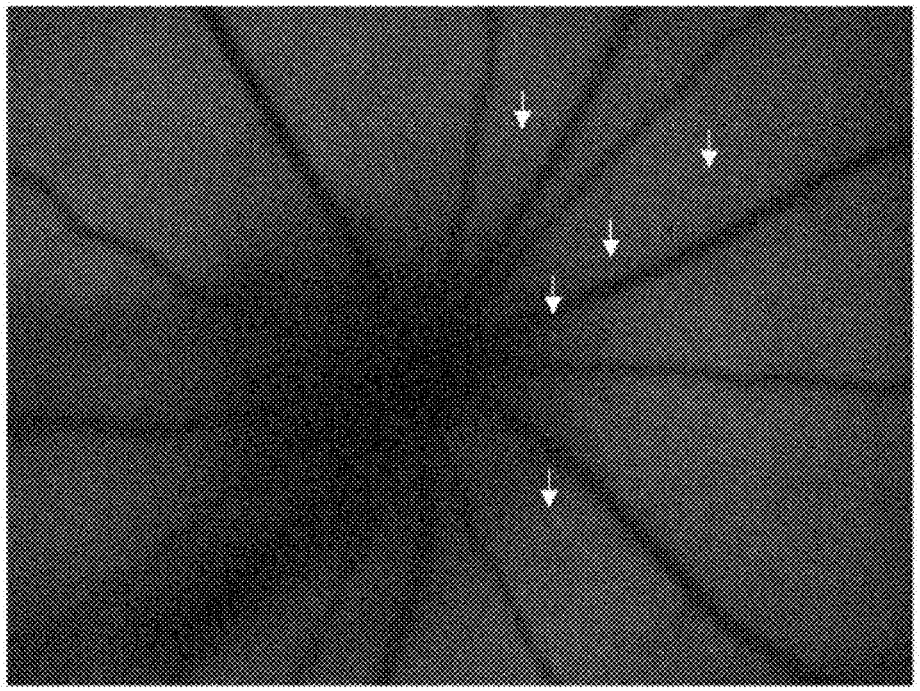
FIG. 6c is a fundus photograph of 60 minutes after Ac-LM-HMRG administration in the PBS group
Figure 6D:
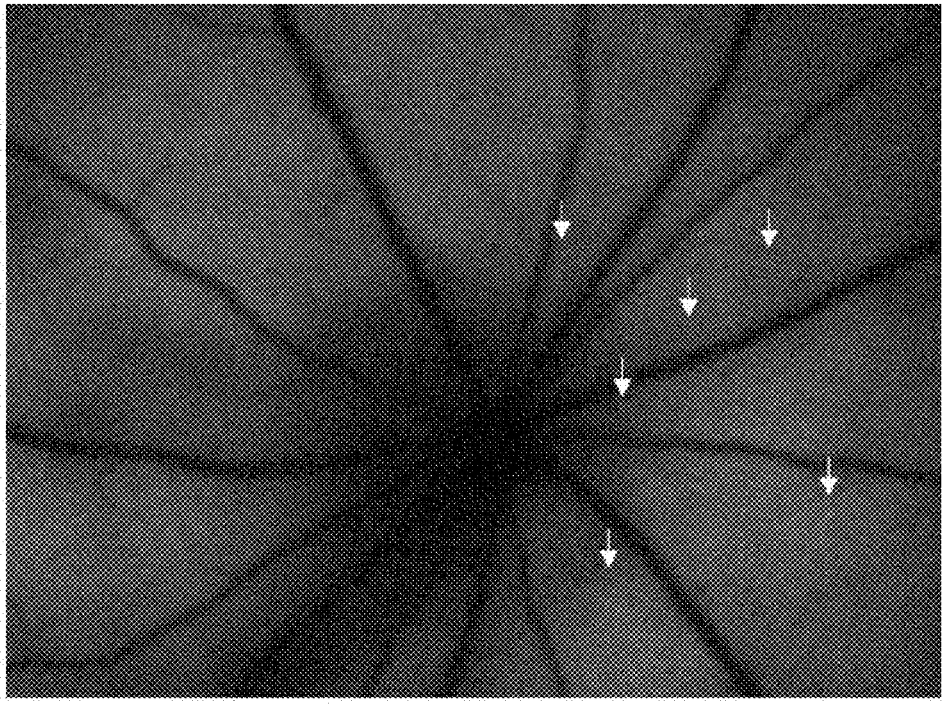
FIG. 6d is a fundus photograph of 90 minutes after Ac-LM-HMRG administration in the PBS group

As shown in FIG. 5a, no clear signal is found before Ac-LM-HMRG administration. However, as shown in FIGS. 5b-5d, nerve cells were clearly stained 30, 60, and 90 minutes after administration of Ac-LM-HMRG in NMDA-administered rats (NMDA group). On the other hand, no signal was found before Ac-LM-HMRG administration in PBS-administered rats (PBS) group (FIG. 6a), and nerve cells were only very slightly stained after 30 minutes (FIG. 6b), 60 minutes (FIG. 6c), and 90 minutes (FIG. 6d).

Given that the rat NMDA injury model is believed to be a retinal disease model, the fluorescent probe of the present invention is believed to be useful in the diagnosis of retinal diseases.

Example 7

Evaluation of Ac-LM-HMRG Using Flat-Mounted Retinas with Mouse NMDA Injury Model (Experimental Procedure)

Figure 7A:
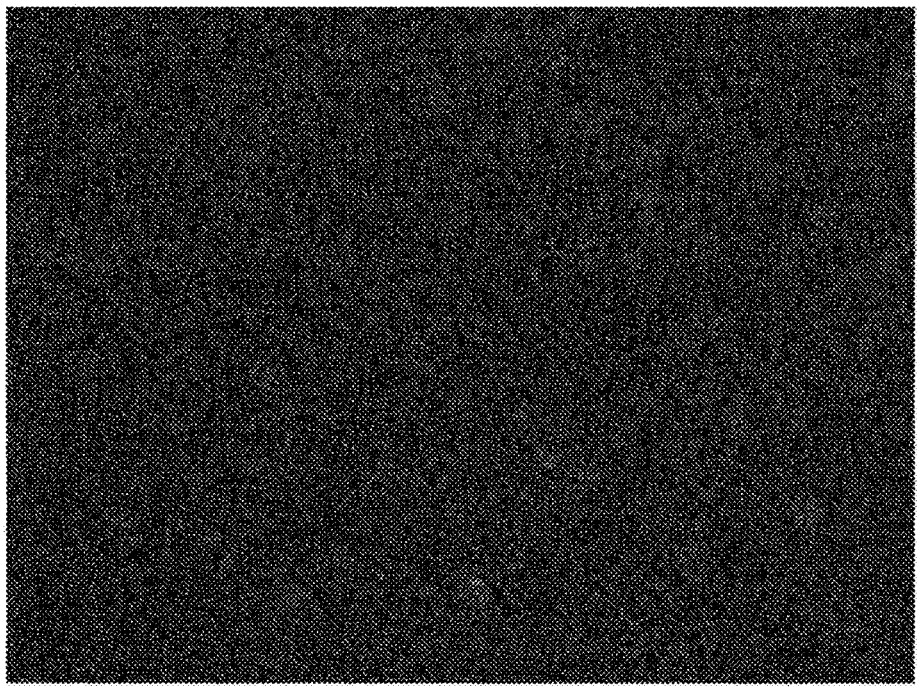
FIG. 7a is an FG stained image of a flat-mounted retina in the NMDA group
Figure 8A:
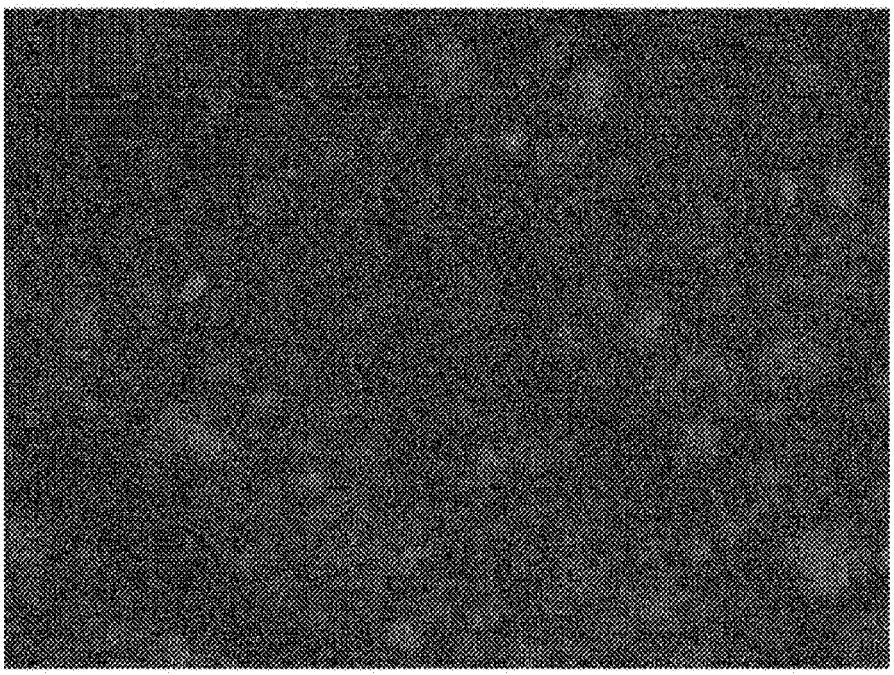
FIG. 8a is an FG stained image of a flat-mounted retina in the PBS group

A study by mouse NMDA injury model was conducted with flat-mounted retinas. First, male BL6/J mice were injected with fluogold (FG), which is a retrograde fluorescent dye tracer, via the superior colliculus, and the retinal ganglion cells were labeled (FIGS. 7a and 8a). After one week, the mice were anesthetized by Nembutal, and 1 μL of 30 mM NMDA (PBS solution) or 1 μL of PBS was administered to the vitreous body in the eye. Two weeks later, the mice were again anesthetized by ketamine-xylazine, and Ac-LM-HMRG (0.5 mM, 1 μL, PBS solution) was administered to the eye. One hour after Ac-LM-HMRG administration, Sytox (registered trademark) Orange (for staining cells that have undergone cell death, 25 μL, 1 μL, PBS solution) (manufactured by Invitrogen) was administered to the vitreous body. Ten minutes later, the eyeball was removed, fixed for two hours by 4% paraformaldehyde (PFA), and flat-mounted retinas were prepared.

The results are shown in FIGS. 7a-7c and FIGS. 8a-8c.

Figure 7B:
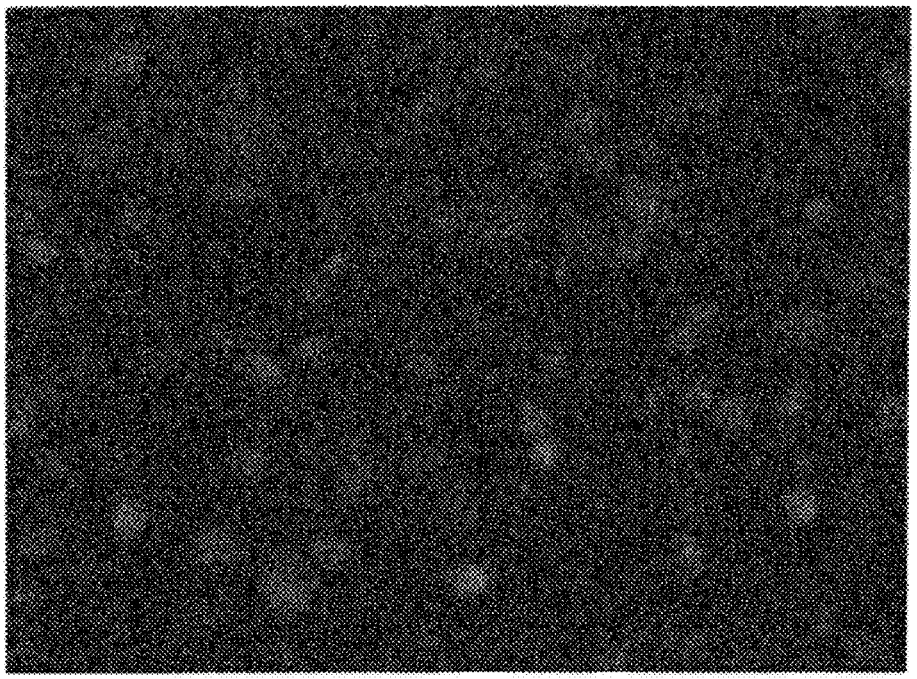
FIG. 7b is an HMRG stained image of a flat-mounted retina in the NMDA group
Figure 7C:
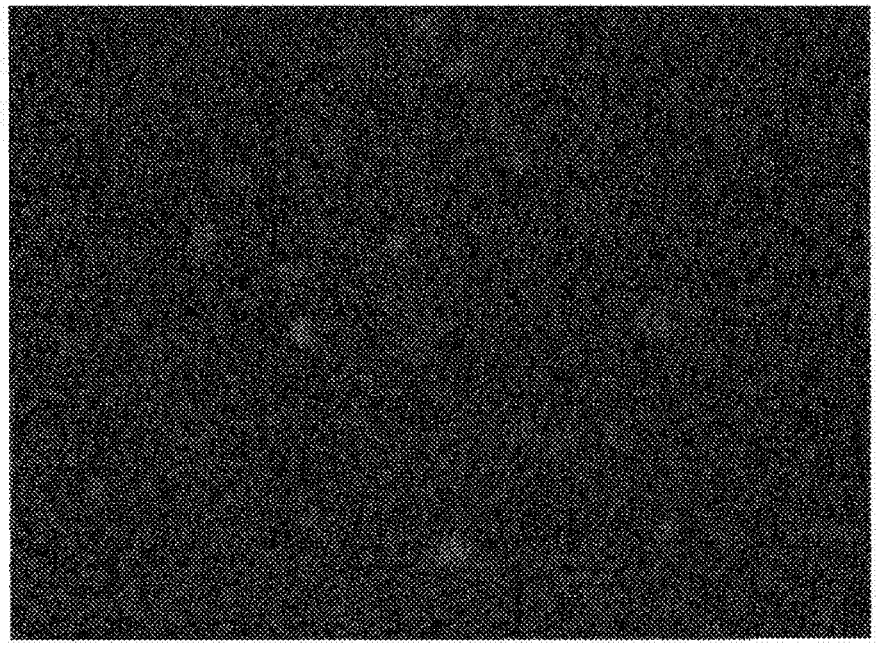
FIG. 7c is a Sytox (registered trademark) Orange stained image of a flat-mounted retina in the NMDA group
Figure 8B:
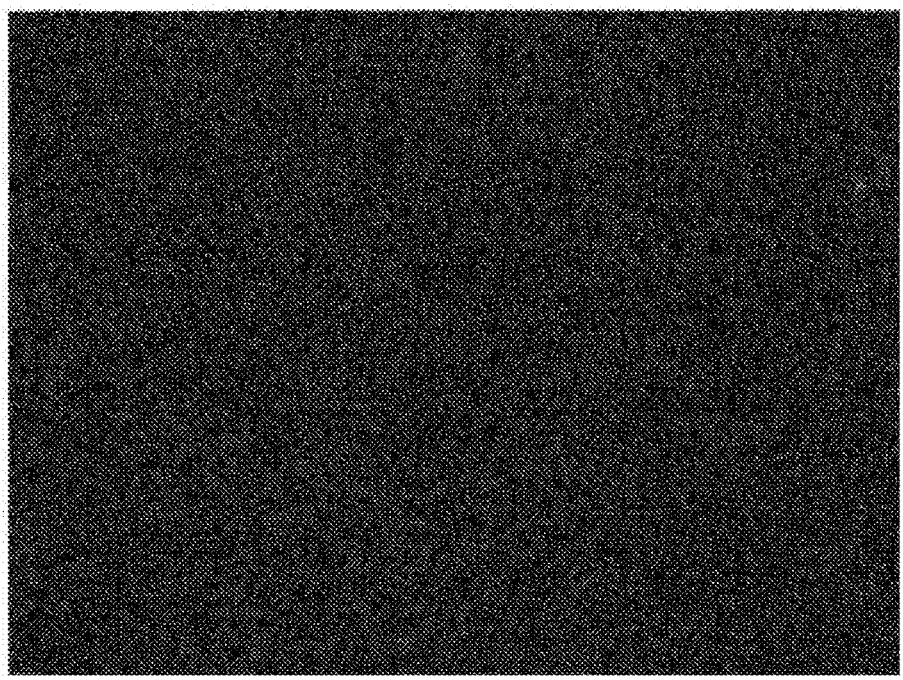
FIG. 8b is an HMRG stained image of a flat-mounted retina in the PBS group
Figure 8C:
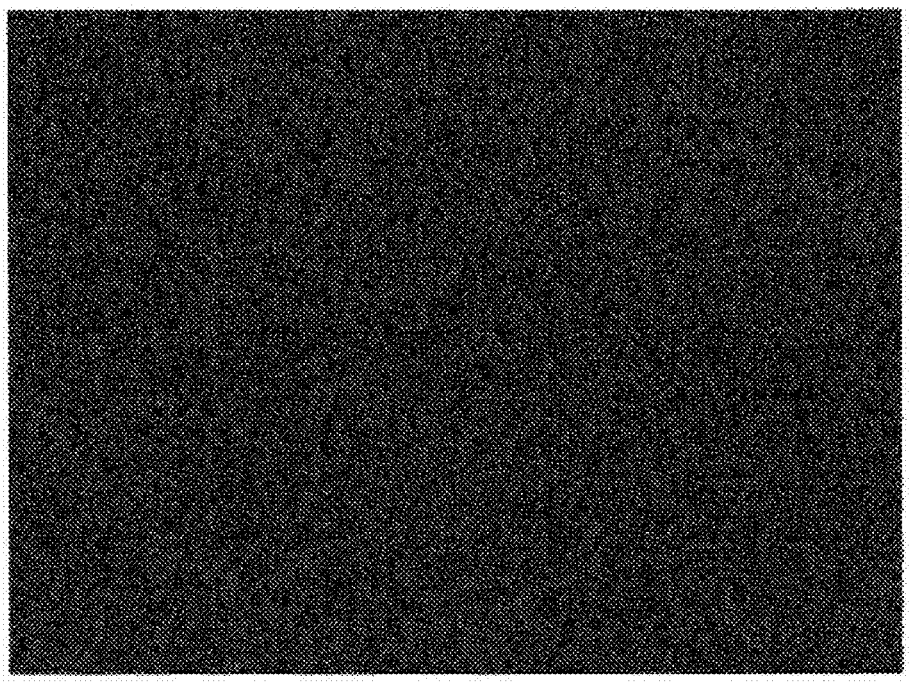
FIG. 8c is a Sytox (registered trademark) Orange stained image of a flat-mounted retina in the PBS group

FIGS. 7a-7c show photographs of flat-mounted retinas of the NMDA group. FIG. 7a shows an FG stained image of the NMDA group, FIG. 7b shows an Ac-LM-HMRG stained image, and FIG. 7c shows a Sytox (registered trademark) Orange stained image. As shown in FIGS. 7b and 7c, calpain activity was detected by Ac-LM-HMRG in the NMDA group, and cell death was also detected. FIGS. 8a-8c show photographs of flat-mounted retinas of the PBS group. FIG. 8a shows an FG stained image of the PBS group, FIG. 8b shows an Ac-LM-HMRG stained image, and FIG. 8c shows a Sytox (registered trademark) Orange stained image. As shown in FIGS. 8b and 8c, images stained by Ac-LM-HMRG and Sytox (registered trademark) Orange were not found since cell death did not occur in the PBS group.

Given that the mouse NMDA injury model is believed to be a retinal disease model, the fluorescent probe of the present invention is believed to be useful in the diagnosis of retinal diseases.

Applying the fluorescent probe of the present invention to patients with retinal diseases such as glaucoma, retinitis pigmentosa, age-related macular degeneration, or retinal neuropathy or retinal vascular occlusive disease associated with diabetes first of all makes it possible to know the calpain activity quickly in the fundus and retinal ganglion cells of the individual patient, which is expected to exert a significant effect in clinical diagnosis and treatment selection. Specifically, the fluorescent probe of the present invention has great medical and industrial value and economic effect, such as prescribing a calpain inhibitor for patients confirmed to have elevated calpain activity.

The invention claimed is:

1. A compound of the following general formula (I):

(I)

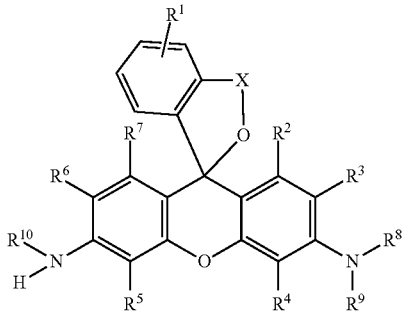

wherein $R^1$ is a hydrogen atom or from one to four of the same or different substituents that bond to the benzene ring;

$R^2$, $R^3$, $R^4$, $R^5$, $R^6$, and $R^7$ are, each independently, a hydrogen atom, hydroxyl group, alkyl group, or halogen atom;

$R^8$ and $R^9$ are, each independently, a hydrogen atom or alkyl group;

X is a $C_1$-$C_3$ alkylene group;

$R^{10}$ is [selected from the following formula (1) or (2);

[

(1)

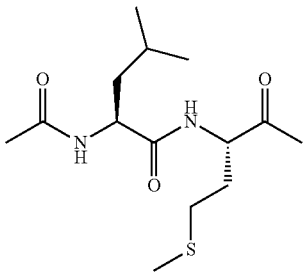

(2)

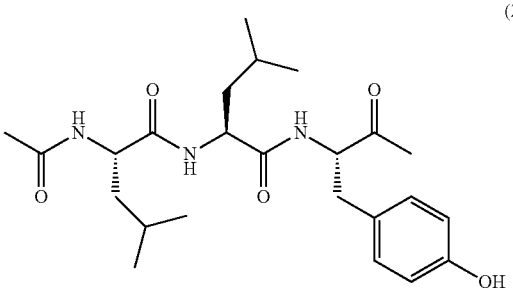

] *a monovalent substituent cleaved by contact with calpain, and said monovalent substituent consists of an oligopeptide residue having a sequence of Leu-Leu-Tyr or Leu-Met (the amino acid at the right end of the sequence bonds directly to the NH group bonded to the xanthene skeleton), the N end of said oligopeptide residue may be protected;* or a salt thereof.

2. A compound of the following formula (3) or a salt thereof (3)

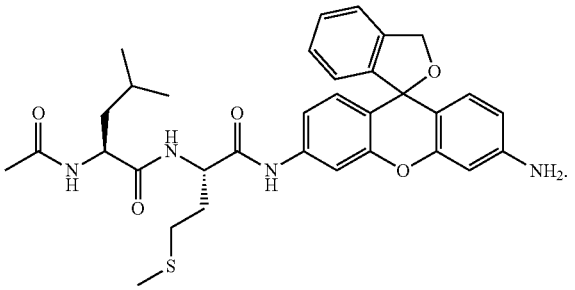

3. A compound of the following formula (4) or a salt thereof (4)

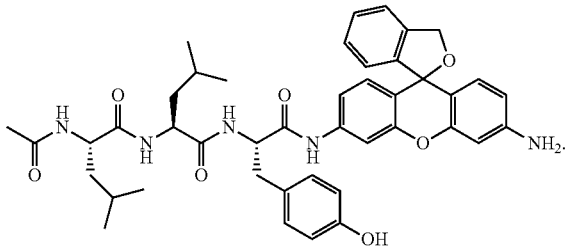

4. A fluorescent probe containing a compound according to claim 1 or a salt thereof.

5. A method for measuring calpain, comprising the following steps: (a) a step for bringing a compound according to claim 1 or a salt thereof and calpain into contact and (b) a step for measuring the fluorescence intensity of the compound produced in step (a) after contact with calpain.

6. A diagnostic for retinal disease containing a compound according to claim 1 or a salt thereof.

7. The diagnostic according to claim 6 wherein the retinal disease is glaucoma, retinitis pigmentosa, age-related macular degeneration, retinal neuropathy or retinal vascular occlusive disease associated with diabetes.

8. The diagnostic according to claim 7 wherein the glaucoma is normotensive glaucoma.

*9. The compound of claim 1, wherein $R^{10}$ is selected from the following formula (1) or (2);*

*(1)*

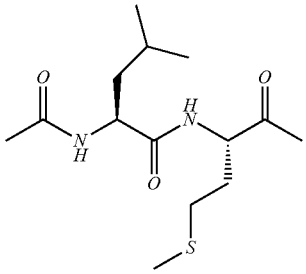

*-continued*
(2)
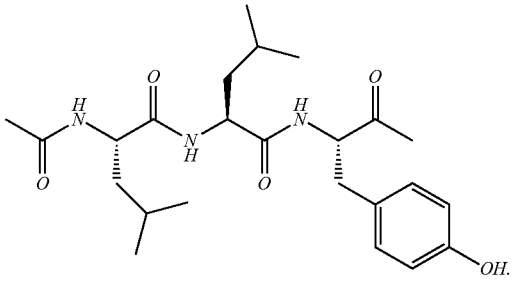
* * * * *